(12) United States Patent
Myers

(10) Patent No.: US 7,584,670 B2
(45) Date of Patent: *Sep. 8, 2009

(54) SYSTEM, APPARATUS AND METHOD FOR TESTING UNDER APPLIED AND REDUCED LOADS

(75) Inventor: Jeffrey Lynn Myers, Middletown, OH (US)

(73) Assignee: General Electric Company, Schnectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/031,916

(22) Filed: Feb. 15, 2008

(65) Prior Publication Data

US 2008/0127744 A1    Jun. 5, 2008

Related U.S. Application Data

(62) Division of application No. 11/002,211, filed on Dec. 3, 2004, now Pat. No. 7,353,715.

(51) Int. Cl.
    *G01N 3/32* (2006.01)
(52) U.S. Cl. .................................................. 73/808
(58) Field of Classification Search ............ 73/808–827
    See application file for complete search history.

(56) References Cited

U.S. PATENT DOCUMENTS 6,938,494 B2 * 9/2005 Takada et al. ................. 73/760

7,353,715 B2 * 4/2008 Myers .......................... 73/837

* cited by examiner

*Primary Examiner*—Max Noori
(74) *Attorney, Agent, or Firm*—V G Ramaswamy; William Scott Andes

(57) ABSTRACT

A system which cyclically applies and reduces a load on a test specimen to thereby subject the test specimen to tensile testing, wherein the system comprises a fluidic mechanical muscle that contracts and extends in length to cyclically apply and reduce the load. This system can use an apparatus comprising: (a) a frame; (b) a load adjusting section associated with the frame and having a fluidic mechanical muscle that contracts and extends in length to cyclically apply and reduce a load; (c) a load train section associated with the frame for subjecting a test specimen to the load; and (d) a lever arm associated with the frame and having load train end adjacent and connected or attached to or otherwise associated with the load train section and a load adjusting end adjacent to and connected or attached to or otherwise associated with the load adjusting section, the lever arm being configured to apply and reduce the load from the loading adjusting section to the load train section. The system and apparatus can be used in a method comprising the following steps: (a) providing a test specimen; and (b) cyclically applying and reducing a load on the test specimen to thereby subject the test specimen to tensile testing, wherein the cyclical application and reduction of the load is caused by the contraction and extension of a fluidic mechanical muscle associated with the load. The system or apparatus can also comprise a mechanism for decoupling at least a portion of the load from the test specimen when the load is reduced.

16 Claims, 7 Drawing Sheets

SYSTEM, APPARATUS AND METHOD FOR TESTING UNDER APPLIED AND REDUCED LOADS

CROSS REFERENCE TO RELATED APPLICATION

This application is a divisional patent application of application Ser. No. 11/002,211, filed Dec. 3, 2004, now U.S. Pat. No. 7,353,715 which is hereby incorporated by reference.

TECHNICAL FIELD OF THE INVENTION

This invention broadly relates to a system, apparatus and method for tensile testing of specimens under applied and reduced loads. This invention particularly relates to a system, apparatus and method for carrying out sustained-peak low cycle fatigue testing of specimens under cyclically applied and reduced loads, especially of materials used in making gas turbine engine components.

BACKGROUND OF THE INVENTION

Evaluating the condition and determining the future performance of mechanical components, such as gas turbine engine components, that operate in the high stress regime of the materials comprising such components, present a challenge because of the complexity of gas turbine components, the materials the components comprise, the variety of in-service operating conditions experienced by the components and the inherent limitations of prevailing remaining useful life, or life expended, estimation methods. Components which operate at high temperatures, such as greater than about 900° F. (482° C.), where a combination of creep and thermal aging of the material constituting the components is of prime concern, demand special consideration in order to achieve an acceptable remaining useful life estimation.

Many systems and methods for testing and estimating the useful life of such components involve applied mechanical loads that vary in time. Of particular interest is low cycle fatigue (LCF) testing, and especially sustained-peak LCF (SPLCF) testing, to examine the fatigue crack growth behavior over time of materials used to make gas turbine engine components. The fatigue crack growth behavior of specimens comprising these materials is characterized by applying cyclic loads using a "creep-rupture" frame. Various cyclic tensile amplitudes are applied, and the number of cycles required to pull apart the specimen under those conditions is recorded. Stress and/or fatigue damage is evidenced by a decrease in strength and stiffness. In some cases, the tests can be terminated after some number of cyclic loadings and then breaking the specimen (i.e., a tensile test) to determine the residual strength. The data from such destructive tests are usually characterized by empirical means and generalized by implication or extrapolation to a variety of service conditions for which the materials were not specifically tested in the laboratory.

In order to fully understand the fatigue behavior of the materials that comprise these specimens as a function of fatigue life, it is desirable to monitor the dynamic response of the specimen continuously over the time of the test. For example, one way to carry out such testing for evaluating fatigue crack growth over time is by using servo-hydraulic testing systems. However, the use of servo-hydraulic testing systems to evaluate long hold-time tests of specimens can be very expensive, especially when multiple specimens are evaluated.

Another, less expensive way to evaluate specimens for long hold-time fatigue and crack growth, as well as other stress-related properties, involves the use of a creep-rupture frame or lever arm tester. See FIG. 1 of U.S. Pat. No. 5,345,826 (Strong), issued Sep. 13, 1994, which schematically illustrates a typical "creep-rupture" frame/lever arm tester. This device consists of a lever arm of from typically twelve to twenty inches in length that is pivotally mounted on a vertical frame at a point along the lever arm's length between its center and an end to which one end of a test specimen is attached. The other end of the test specimen is attached to a fixed base plate. When weights are applied or loaded on the opposite end of the lever arm, a tensile force is exerted on the test specimen according to the formula $t=(wl)/d$, where $t$ is the tensile force exerted on the test specimen, $w$ is the weight applied to the far end of the lever arm, $l$ is the distance between the lever arm pivot point and the end carrying the applied weights, and $d$ is the distance between the lever arm pivot point and the end connected to the test specimen. The applied force, $t$, causes tensile testing of the specimen to take place.

Creep-rupture frames/lever arm testers can be equipped to cyclically apply and reduce the load (e.g., created by the weights) on the test specimen. Previously, the cyclical application and reduction of the load in creep-rupture frames/lever arm testers was carried out by using either a standard pneumatic cylinder or a scissor jack lift. With a standard pneumatic cylinder, the load is repeatedly applied and reduced by the respective contraction and extension of the length of the cylinder through pressurization and depressurization with air. The disadvantage of using a standard pneumatic cylinder for cyclical application and reduction of the load is that contraction and extension of the cylinder is generally dynamic. Of particular concern is that standard pneumatic cylinders, especially over time, exhibit a "stiction" phenomena such that contraction and extension of the cylinder is not always smooth, but can occur as a series of jerky, unpredictable motions because the cylinder seals temporarily stick. This has been found to be due to the seal material in the cylinder migrating into the walls thereof over time. In addition, it is more difficult to control the dynamic contraction and expansion of a standard pneumatic cylinder, and it is thus more difficult to control the application and reduction of the load.

With a scissor jack lift, the load is repeatedly applied and reduced by having the jack expand or collapse vertically in an accordion-like fashion. The disadvantage of using a scissor jack lift is that expansion/collapse is relatively slow. The scissor jack lift is also mechanically limited in that it is not designed for such cyclical use. In addition, the scissor jack lift requires a high degree of maintenance for use in cyclical application and reduction of load, and can therefore be expensive and time consuming to operate.

Accordingly, there exists a need for a system, apparatus and method for cyclical application and reduction of loads in tensile testing of specimens that allows for a relatively smooth application and reduction of the applied loads. There also exists a need for a system, apparatus and method for cyclical application and reduction of loads in tensile testing of specimens that allows for a more easily controlled application and reduction of the load. There further exists a need for a system, apparatus and method for cyclical application and reduction of loads in tensile testing of specimens that is responsive to the need to apply and reduce the load fairly quickly, and that does not require a high degree maintenance thereof over time.

BRIEF DESCRIPTION OF THE INVENTION

An embodiment of this invention is broadly directed at a system which cyclically applies and reduces a load on a test specimen to thereby subject the test specimen to tensile testing, wherein the system comprises a fluidic mechanical muscle that contracts and extends in length to cyclically apply and reduce the load.

Another embodiment of this invention is broadly directed at an apparatus, which comprises:
 a. a frame;
 b. a load adjusting section associated with the frame and having a fluidic mechanical muscle that contracts and extends in length to cyclically apply and reduce a load;
 c. a load train section associated with the frame for subjecting a test specimen to the load; and
 d. a lever arm associated with the frame and having a load train end adjacent and connected to the load train section and a load adjusting end adjacent and connected to the load adjusting section, the arm being configured to apply and reduce the load from the load adjusting section to the load train section.

Another embodiment of this invention is broadly directed at a method comprising the following steps:
 (a) providing a test specimen; and
 (b) cyclically applying and reducing a load on the test specimen to thereby subject the test specimen to tensile testing, wherein the cyclical application and reduction of the load is caused by the contraction and extension of a fluidic mechanical muscle associated with the load.

Another embodiment of this invention is broadly directed at a system or apparatus which cyclically applies and reduces a load on a test specimen to thereby subject the test specimen to tensile testing, wherein the system or apparatus comprises a mechanism for decoupling at least a portion of the load from the test specimen when the load is reduced.

The system, apparatus and method of this invention provides several benefits and advantages. The fluid mechanical muscle used in the system, apparatus and method of this invention allows for an automatic and relatively smooth application and reduction of the load (e.g., without the occurrence of a "stiction" phenomena) in the cyclical tensile testing of specimens. The fluid mechanical muscle used in the system, apparatus and method of this invention also allows for a more easily controlled application and reduction of the load. The fluid mechanical muscle used in the system, apparatus and method of this invention is relatively easy to maintain over time and can be integrated into existing creep-rupture systems when needed without significantly altering the original configuration or function of the creep-rupture system. The system, apparatus and method of this invention is also relatively inexpensive in comparison to servo-hydraulic systems in carrying out various types of cyclic fatigue tensile testing, especially on multiple specimens.

DETAILED DESCRIPTION OF THE INVENTION

Figure 1:
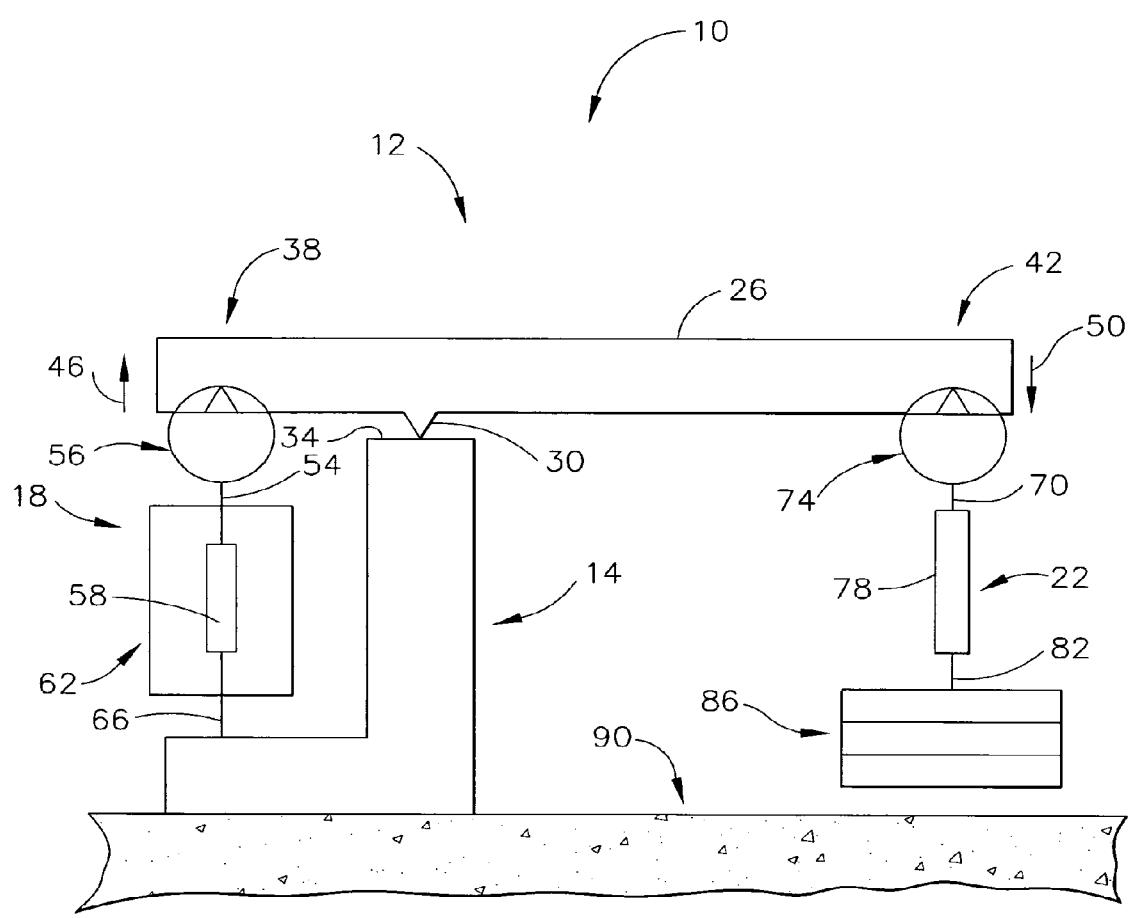
FIG. 1 is a schematic view of an "open loop" system embodiment of this invention.

As used herein, the term "load" refers to any mass, weight, force, etc., to which a test specimen is subjected to by a system, apparatus and/or method of this invention.

As used herein, the term "applying the load" refers to subjecting the test specimen to a load, including increasing the amount or degree of load that the specimen is subjected to.

As used herein, the term "reducing the load" refers to partially or completely decreasing, diminishing, eliminating, etc., the load the test specimen is subjected to.

As used herein, the term "cyclically applying and reducing a load" refers to at least one cycle where the load is applied and reduced, in any order thereof, i.e., apply and reduce load, reduce and apply load, etc. Typically, the cycle involves first applying the load progressively or sequentially, and subsequently reducing the load progressively or sequentially. The cyclic application and reduction of the load can be a single cycle, or more typically is a plurality of such cycles (i.e., for at least two cycles). The load can be applied and reduced in the same manner or pattern each cycle, or can be applied and reduced in a different manner or pattern each cycle. The load can also be applied and held (i.e., sustained) at a specified level (i.e., the load is neither increasing nor decreasing) for the same or different discrete period of time one or more times during the cycle, can be increased and/or can be decreased progressively or sequentially at the same or different rates, or any combination thereof, during each cycle.

As used herein, the term "closed loop system" refers to a control system having a feedback mechanism (e.g., a mechanical and/or electronic signal or plurality of signals) for adjusting, altering, controlling, etc., the application and/or reduction of the load on the test specimen. The feedback mechanism used in a closed loop system typically provides a substantially linear and proportional application and/or reduction of the load on the test specimen.

As used herein, the term "open loop system" refers to a control system that does not utilize a feedback mechanism.

As used herein, the terms "creep-rupture frame" and "lever arm tester" refer interchangeably to a device that typically comprises a lever arm of mechanical advantage typically from about twelve to about twenty inches (from about 30.5 to about 51 cm.) in length that is pivotally supported on a fixed vertical member of a frame at a point along the lever arm's length between its center and an end to which one end of a test specimen is attached, with the other end of the test specimen typically being attached to a base plate or platform (e.g., of a cross-frame), and where one or more weights are applied or loaded on the opposite end of the lever arm. See FIG. 1 and the corresponding description in U.S. Pat. No. 5,345,826 (Strong), issued Sep. 13, 1994 (herein incorporated by reference), which schematically illustrates a typical "creep-rupture" frame/lever arm tester. Suitable creep-rupture frame/lever arm testers for use herein include those made by SATEC, ATS, etc.

As used herein, the term "fluidic mechanical muscle" refers to a device which typically contracts in length in a relatively controlled manner upon being pressurized with a fluid (i.e., a gas such as air or a liquid such as ethylene glycol) and extends in length in a relatively controlled manner upon the release of the pressurized fluid. In the system, apparatus and method of this invention, contraction of the fluidic mechanical muscle typically causes the application of the load to the test specimen, while the extension of the fluidic mechanical muscle typically causes the reduction of the load. The fluidic mechanical muscle has characteristics such that when it is pressurized, the relative length of the muscle typically contracts substantially linearly with the applied pressure while at the same time creating substantial forces suitable for actuating, lifting, moving, positioning, etc, the load, and conversely extends substantially linearly with the reduction (release) of pressure.

Because of their different construction, and especially their inherent non-dynamic, relatively controlled contraction and extension in length, the fluidic mechanical muscles useful herein differ from standard dynamic pneumatic cylinders. Fluidic mechanical muscles suitable for use herein can be of the "McKibben" type of fluid contractile actuator or "muscle" that typically includes a cylindrical sheath formed from a flexible mesh (sometimes referred to as a "braiding" structure) comprising a plurality of interconnected rhomboidal or rhombus shaped segments that are secured to connectors at each end of the sheath with a bladder comprising a strong expandable material disposed within the sheath, and with an inflation line connected to the bladder through which a pressurizing fluid may be introduced for the purpose of inflating or expanding the bladder within the cylindrical sheath, along with appropriate valves on the inflation line to direct fluid from a pressurizing source into the bladder for inflation (contraction), as well as to allow fluid to escape from the bladder for release/deflation (extension) See, for example, U.S. Pat. No. 4,739,692 (Wassam et al), issued Apr. 26, 1988 (herein incorporated by reference), which describes the operation of a "McKibben" type of fluid contractile actuator or "muscle." In operation, the "McKibben" type fluidic contractility actuator or "muscle" is connected between two fixed points using a connector with the bladder deflated. The cylindrical sheath formed from the flexible mesh is connected between two flexible points and ideally experiences a very slight tensile stress in order to ensure that the sheath when connected in its extended or "relaxed" position between the two points is at a minimum diameter. The inflation line is connected to the source of pressurizing fluid that may be compressible, i.e., a gas, or incompressible, i.e., a liquid. The fluid when introduced into the bladder expands it against the enclosing mesh sheath, causing it to expand diametrically and contract longitudinally generating an extremely large contractile force between the connectors. See also U.S. Pat. No. 4,615,260 (Takagi et al), issued Oct. 7, 1986; U.S. Pat. No. 5,158,005 (Negishi et al), issued Oct. 27, 1992; U.S. Pat. No. 5,165,323 (Sato), issued Nov. 24, 1992; and U.S. Pat. No. 5,201,262 (Negishi et al), issued Apr. 13, 1993 (herein incorporated by reference), as well as U.S. Pat. No. 4,841,845 (Beullens), issued Jun. 27, 1989; U.S. Pat. No. 6,067,892 (Erickson), issued May 30, 2000; and U.S. Pat. No. 6,223,648 (Erickson), issued May 21, 2001 (herein incorporated by reference), for other fluidic mechanical muscles of the "McKibben" type of fluid contractile actuator or "muscle" that are potentially suitable for use herein. Examples of commercially available fluidic mechanical muscles suitable for use herein include those made by Festo Corporation of the "Fluidic Muscle MAS" series, including Model No. MAS-10-N-AA-MCFK, Part 187594; Model No. MAS-10-N-AA-MOFK, Part 187595; Model No. MAS-40-N-459-AA-MCIK, Part 187605; Model No. MAS-40-N-AA-MCIK, Part 187606); Model No. MAS-40-N-AA-MOKK, Part 187607; Model No. MAS-20-N-AA-MCHK, Part 187617; Model No. MAS-20-N-AA-MCGK, Part 187618; Model No. MAS-20-N-AA-MOHK, Part 187619; Model No. MAS-10-, Part 534201; Model No. MAS-20-, Part 534202; and Model No. MAS-40-, Part 534203, etc.

As used herein, the term "test specimen" refers to any specimen, including a component, part, etc., comprising a material of interest, or a specimen fabricated, manufactured, etc., from a material of interest that is subjected to a load by the system, apparatus and/or method of this invention. The test specimen can be of any suitable shape or configuration, including rectangular, cylindrical, etc. Typically, the test specimen has a reduced gauge or width at the middle section thereof (e.g., is "dog-bone shaped") to force elongation of the material at the middle of the specimen when subjected to the load.

As used herein, the terms "tension testing" and "tensile testing" refer interchangeably to a test format where the test specimen is subjected to a substantially longitudinal stretching, pulling, etc, force when the load is applied thereto. Representative, but non-limiting examples of tension or tensile testing include low cycle fatigue testing, sustained-peak low cycle fatigue testing, creep-rupture testing, high strain rate peak testing, bend testing, crack growth testing, etc.

As used herein, the terms "low cycle fatigue testing" or "LCF testing" refer interchangeably to a slower or lower loading cycle speed fatigue type test where the cycle is usually about 30 Hertz or less, and is typically in the range of from about 0.3 to about 1 Hertz.

As used herein, the terms "sustained-peak low cycle fatigue testing" or "SPLCF testing" refer interchangeably to a type of LCF test where the peak load applied to the test specimen is held or sustained at a specified level for a discrete period of time.

As used herein, the term "bend testing" refers to a test format where the test specimen is supported at its respective ends and the load is applied proximate to the midpoint thereof between the respective ends.

As used herein, the terms "mission cycle testing" or "simulation testing" refer interchangeably to testing that is intended to represent an actual operation (i.e., real life phenomena) and is typically carried out using a closed loop test system. Mission cycle/simulation testing typically refers to a type of field testing (e.g., of an engine) where the engine is operated, data is taken and brought back to a mission or simulator operation lab (either manually or more typically electronically), and the data is then used to program (typically using a computer), for example, a simulated, but real life stress cycle on the test specimen of interest.

As used herein, the term "creep-rupture test" refers to a test format where a static and consistent load is applied to the test specimen and where the elongation of the test specimen during the application of the load is measured.

As used herein, the term "fracture toughness" refers to the measurement of the resistance of a specimen being tested to extension of a crack. See Davis, ASM Materials Engineering Dictionary (1992), p. 72.

As used herein, the term "fatigue crack growth test" refers to a test format that measures of the rate of growth of a crack in a test specimen over time or over an applied load cycle(s).

Referring now to the drawings, FIG. 1 is a schematic view of an "open loop" tensile testing system indicated generally as 10 that uses a tensile testing apparatus in the form of a lever arm tester 12. Tester 12 includes a generally L-shaped frame indicated as 14, a generally vertically extending load train section indicated as 18 and associated with frame 14, a generally vertically extending load adjusting section indicated as 22 and associated with frame 14, and a mechanism for applying and reducing a load from the load adjusting section 22 to the load train section 18, and to thus cause the load to be applied (typically in the form of tensile stress) or reduced on the test specimen of interest, in the form of a pivoting generally horizontally extending boom or lever arm 26. Lever arm 26 includes a fulcrum or pivot point 30 for balancing arm 26 on the top end 34 of the longer length vertical segment of frame 14 about which arm 26 swings or pivots. Lever arm 26 also has a load train end indicated as 38 and a load adjusting end indicated as 42. As shown in FIG. 1 and as illustrated by upward pointing arrow 46 and downward pointing arrow 50, respectively, as load adjusting end 42 of arm 26 moves, for example, generally downwardly about a generally horizontally axis defined by pivot point 30, the load train end 38 moves generally upwardly, and vice versa when load adjusting end 42 moves generally upwardly about the horizontal axis defined by pivot point 30. The particular position of pivot point 30 along the length of arm 26 between ends 38 and 42 can be moved horizontally and determines the multiple of load effectively transferred by arm 26 from the load adjusting section 22 to the load train section 18, as represented by the formula t=(wl)/d, where t is the tensile force exerted on the test specimen, w is the weight or load applied to the load adjusting end 42 of the lever arm 26, l is the distance between pivot point 30 and load adjusting end 42, d is the distance between pivot point 30 and load train end 38 connected or attached to or otherwise associated with the test specimen, and where the applied force, t, imparts a stress to the test specimen. The closer pivot point 30 is to load train end 38, and conversely away from load adjusting end 42 (i.e., d is smaller and l is larger), the greater the multiple of load that is effectively transferred or applied from load adjusting section 22 to load train section 18, i.e., the greater the value for t. For example, a load (w) of 10 units in load adjusting section 22 can be translated by arm 26 into a force (t) of 200 units applied to load train section 18 (and test specimen) if the ratio of l:d is 20:1.

As shown in FIG. 1, load train section 18 includes an upper pull rod 54 that is adjacent to and is connected or attached to or otherwise associated at its upper end as indicated generally by 56 with load train end 38 of arm 26, and that is also adjacent to and is connected or attached to or otherwise associated at its lower end thereof with a test specimen indicated generally as 58. Load train section 18 can also include an environmental chamber such as a furnace indicated generally as 62 which encloses specimen 58. Load train section 18 further includes a lower pull rod indicated generally as 66 that is adjacent to and is connected or attached to or otherwise associated at its upper end with specimen 58, and that is also adjacent to and is connected or attached to or otherwise associated at its lower end with frame 14. Because upper pull rod 54 is vertically movable and especially moves upwardly when load train end 38 of arm 26 pivots upwardly in the direction indicated by arrow 42, and because the lower pull rod 66 remains essentially stationary by being attached to frame 14, test specimen 58 is subjected to a tensile force, typically in the form of a strain or stress.

As shown in FIG. 1, the load adjusting section 22 includes an upper connector 70 that is adjacent to and is connected or attached to or otherwise associated at its upper end with load adjusting end 42 of arm 26 as indicated generally by 74. Load adjusting section 26 also includes a fluidic mechanical muscle indicated generally as 78 that is adjacent to and is connected or attached or otherwise associated at its upper end with the lower end of connector 70. As muscle 78 contracts in length, the load in load adjusting section 22 is applied (via arm 26) to load train section 18, and conversely, as muscle 78 extends in length, the load in load adjusting section 22 is reduced (via arm 26) on load train section 18. Load adjusting section 22 further includes a lower connector 82 that is adjacent to and is connected or attached to or otherwise associated at its upper end with the lower end of muscle 78, and is also adjacent to and is connected or attached to or otherwise associated at its lower end with a load indicated generally as 86. As also shown FIG. 1, load 86 is above the ground or main surface 90, thus indicating that system 10 is at a point in the testing cycle where muscle 78 is in a contracted state and where load 86 is thus being applied (via arm 26 and load train 18) to specimen 58.

Figure 2:
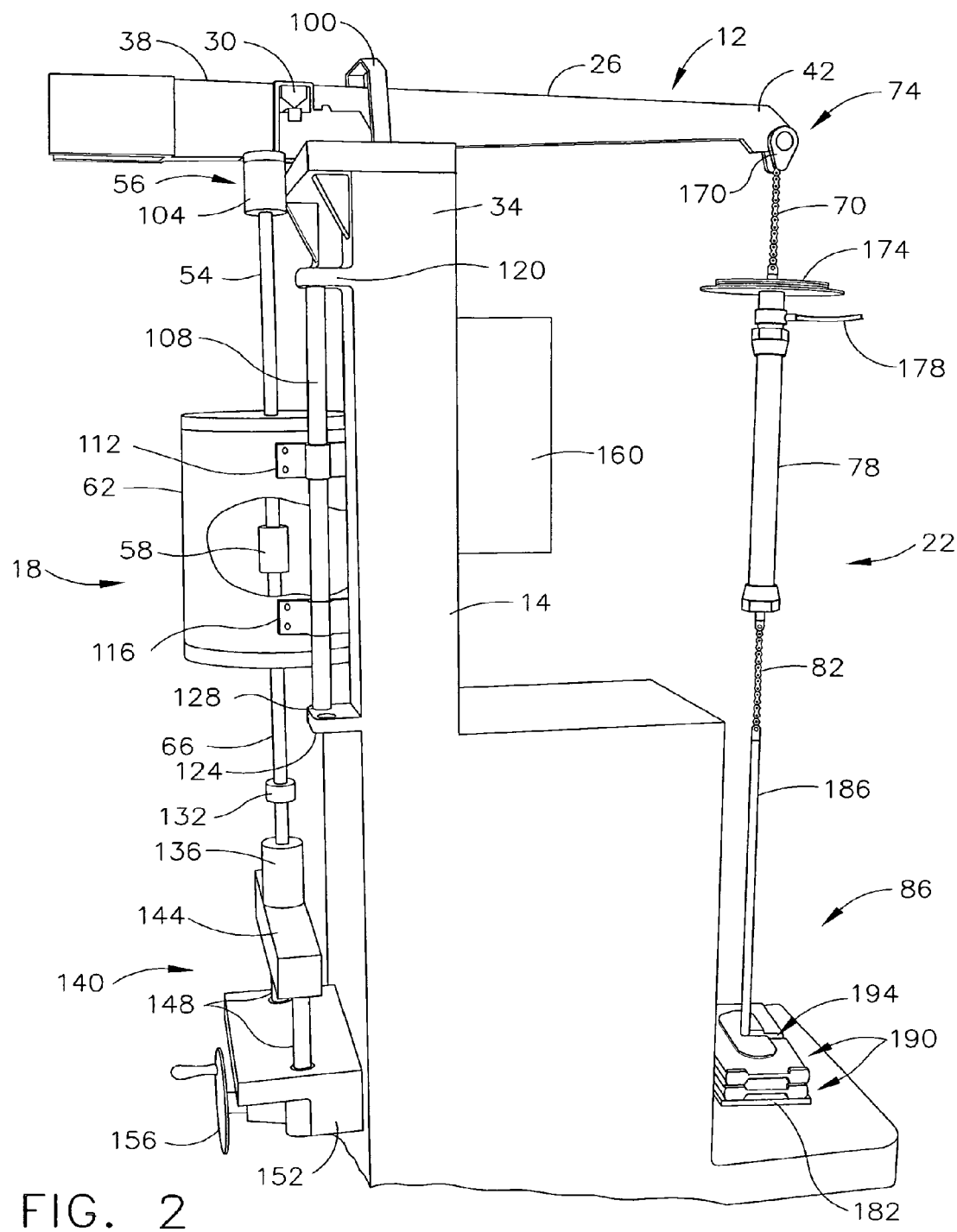
FIG. 2 is a more detailed perspective view with portions broken away of the apparatus that can be used in the "open loop" system of FIG. 1.

Referring to FIG. 2 where the further details of lever arm tester 12 are shown, a generally U-shaped containment bracket 100 is provided and attached to the top end 34 of frame 14 to keep arm 26 from pivoting or swinging too much up or down about pivot point 30 and especially to prevent arm 26 from potentially falling off of frame 14. An upper universal joint 104 is used at point 56 to connect or attach the upper end of upper pull rod 54 to the load train end 38 of arm 26. A generally cylindrical mounting column 108 is attached to or mounted on furnace 58 by a spaced apart pair of hinges indicated as upper hinge 112 and lower hinge 116. Column 108 is pivotally mounted to frame 14 by an upper bracket 120 having a circular recess (not shown) for receiving the upper end of column 108 and a lower bracket 124 also having a circular recess 128 for receiving the lower end of column 108. An inline load cell 132 is mounted on lower pull rod 66 between the respective upper and lower ends thereof to directly measure the load being applied to test specimen 58. A lower universal joint 136 connects or attaches the lower end of lower pull rod 66 to a vertically movable cross-head assembly indicated generally as 140. Cross-head assembly 140 includes a generally horizontally extending cross-head 144 connected or attached to or otherwise associated with a generally vertically extending and spaced apart pair of rods 148 that are connected or attached to or otherwise associated with a generally horizontally extending base or platform 152. A manual turn crank 156 is mounted on platform 152 for vertically moving or adjusting the position of load train section 18 either upwardly or downwardly relative to frame 14. A furnace control box indicated generally as 160 that is mounted on frame 14 and that is connected to furnace 62 by control cables or lines (not shown) is used to control the environmental conditions (e.g., temperature, pressure, gas surrounding specimen 58, etc.) within furnace 62.

As also shown in FIG. 2, a pivoting connector 170 is used at point 74 to connect or attach load adjusting end 42 of arm 26 to upper connector 70 in the form a flexible link or chain. Chain 70 is connected or attached to or otherwise associated with an R-ratio or minimum load pan 174. Load pan 174 is connected or attached to or otherwise associated with the upper end of fluidic mechanical muscle 78 that is shown as having a fluid inlet and outlet line 178 for pressurizing and depressurizing muscle 78. The lower end of muscle 78 is connected or attached to or otherwise associated with lower connector 82 in the form of a flexible link or chain. Because chain 82 is flexible, it provides sufficient slack when muscle 78 is in an extended state so that load 86 is completely or substantially completely reduced, i.e., there is no force or stress exerted by load 86 on test specimen 58. In other words, chain 82 provides a mechanism for decoupling (e.g., mechanical decoupling) at least the principal portion of the load (i.e., load 86) from test specimen 58 when the load is reduced during that portion of the testing cycle. Chain 82 is connected or attached to or otherwise associated with load 86 that includes a generally horizontally extending weight platform 182 and an elongated weight receiving rod 186 connected or attached to or otherwise associated with platform 182 and extends generally vertically upwardly therefrom and is then connected or attached to or otherwise associated with chain 82. As shown in FIG. 2 one or more weights 190 of similar or different mass can be loaded onto platform 182 and are configured with a slot 194 so that weights 190 can be securely receive by elongated rod 186.

Figure 3:
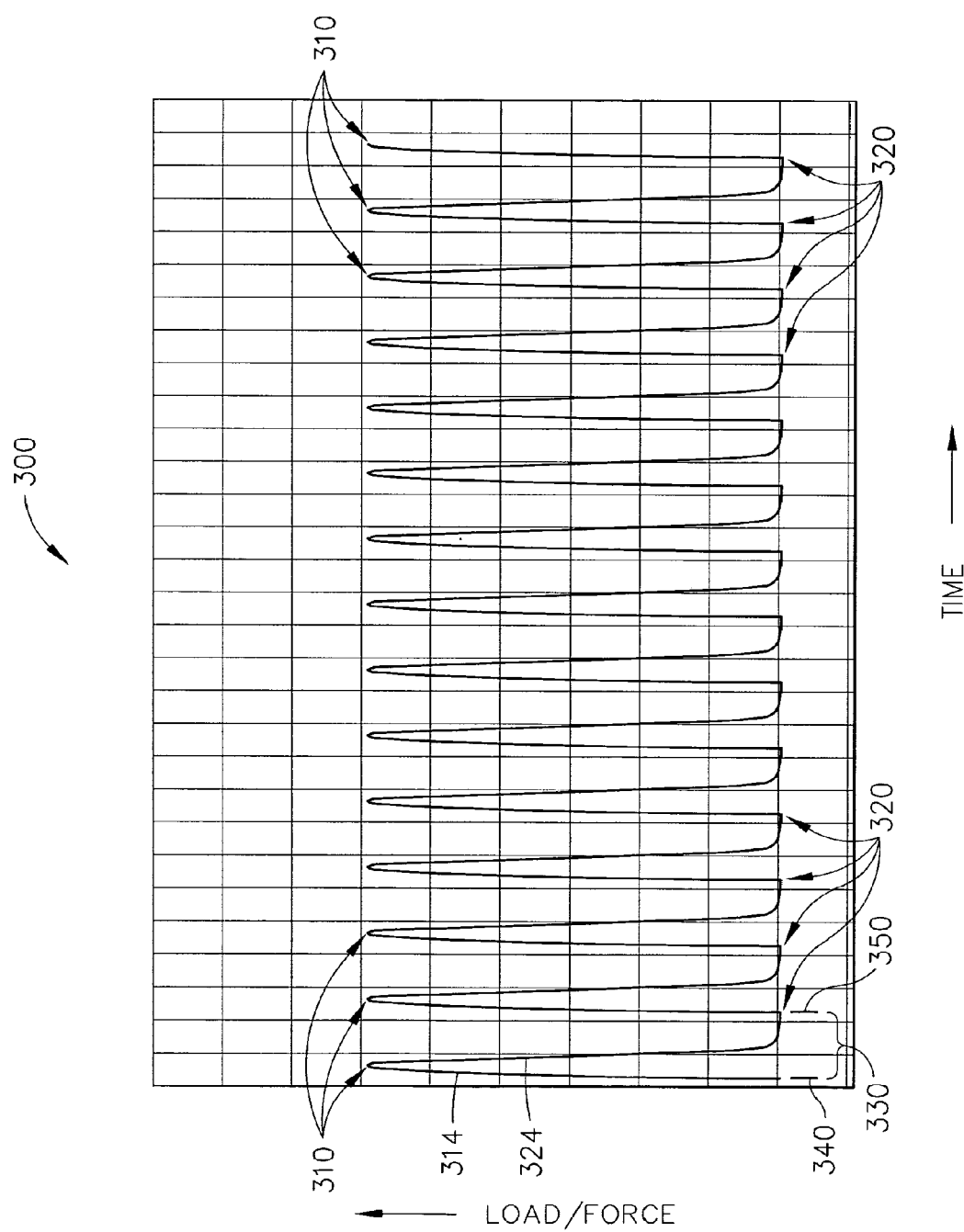
FIG. 3 is an illustrative graphical plot of a low cycle fatigue test that can be carried out using the system and apparatus of FIGS. 1 and 2.

FIG. 3 is an illustrative graphical plot indicated generally as 300 of a low cycle fatigue (LCF) test that can be carried out using the system and apparatus of FIGS. 1 and 2. As shown in FIG. 3, graphical plot 300 of the LCF test has a series of peaks indicated as 310 which represent the peak application of the load on the test specimen along the portions of plot 300 indicated by upward slope 314 during the loading (i.e., load increasing) phase of a test cycle, as well as valleys indicated as 320 which represent the reducing of the load on the test specimen along the portions of plot 300 indicated by downward slope 324 during the reducing (load decreasing) phase of a test cycle. As shown in FIG. 3, the application and reduction of the load in an LCF test is typically relatively rapid. As also shown in FIG. 3, valleys 320 do not reach the base line because of the minimum load applied or sustained by load pan 174. Because of the repeated application and reduction of the load in the LCF test, graphical plot 300 represents a plurality of cycles where the load is applied and then reduced. One such cycle is indicated as 330 in FIG. 3 and has a start point indicated by 340 and an end point indicated by 350.

Figure 4:
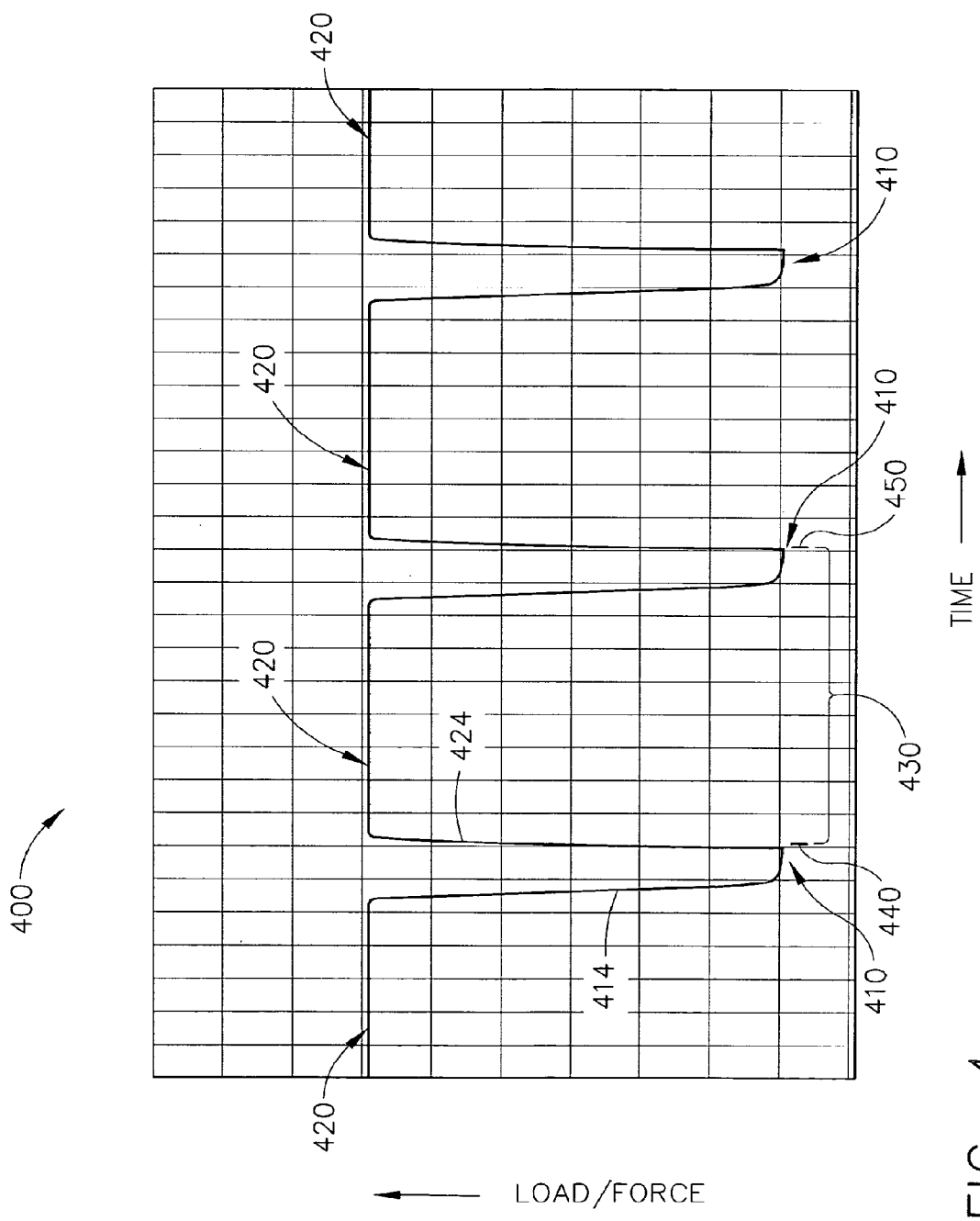
FIG. 4 is an illustrative graphical plot of a sustained-peak low cycle fatigue test that can be carried out using the system and apparatus of FIGS. 1 and 2.

FIG. 4 is an illustrative graphical plot indicated generally as 400 of a sustained-peak low cycle fatigue (SPLCF) test that can be carried out using the system and apparatus of FIGS. 1 and 2. As shown in FIG. 4 and like FIG. 3, graphical plot 400 of the SPLCF test has a series of valleys indicated as 410 which represent the reduction of the load on the test specimen along the portions of plot 400 indicated by downward slope 414 during the reducing (load decreasing) phase of a test cycle. As also shown in FIG. 4 and unlike FIG. 3, graphical plot 400 has a series of plateaus indicated as 420 which represent the sustained application (holding) of the peak load on the test specimen after that portion of plot 400 indicated by upward slope 424 representing the loading (load increasing) phase of a test cycle. As shown in FIG. 4, the application and reduction of the load in an SPLCF test is relatively rapid, but unlike the LCF test in FIG. 3, the application of the peak load (see plateaus 420) in the SPLCF test is held or sustained at specified level for a given or discrete period of time. Because of the repeated application and reduction of the load in the SPLCF test, graphical plot 400 represents a plurality of cycles where the load is applied, held/sustained and then reduced. One such cycle is indicated as 430 in FIG. 3 and has a start point indicated by 440 and an end point indicated by 450.

Figure 5:
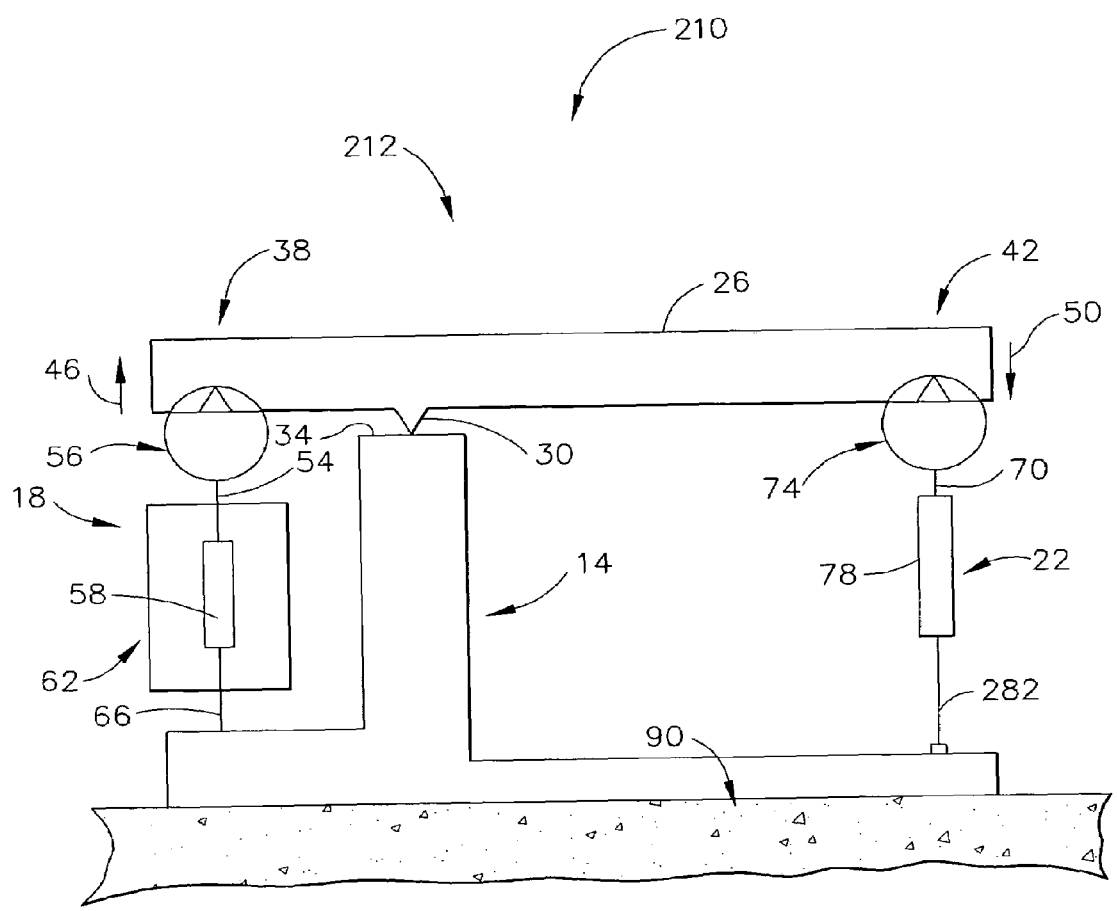
FIG. 5 is a schematic view of a "closed loop" system embodiment of this invention.

FIG. 5 shows a "closed loop" system embodiment of this invention indicated generally as 210 which differs primarily from "open loop" system 10 of FIG. 1 in that there is no adjustable load 86. Instead, fluidic mechanical muscle 78 of tester 212 is directly connected or attached to or otherwise associated with frame 14 by use of a connector such as link or chain 282. See also FIG. 6 which provides a more detailed view of lever arm tester 212 that can be used in such as "closed loop" system 210 where chain 282 is directly connected or attached to or otherwise associated with frame 14.

The "closed loop" system 210 is typically used for mission cycle or simulation testing that is based on control of the test by a computer program that is derived from data from field tests of actual components, parts, materials, or operating equipment, e.g., a gas turbine engine. For example, the controller (not shown) for the fluidic mechanical muscle 78 can get a signal from the computer program to apply a specific load to the test specimen, as a result of which the muscle 78 contracts in response thereto to apply the load. The controller also receives a feedback signal from load cell 132 indicating how much load is currently being applied to the test specimen 58. Until load cell 132 senses an applied load to the test specimen equal to that specified by the controller to muscle 78, muscle 78 will continue to contract and apply load. When load cell 132 senses an applied load to the test specimen that is equal to that specified by the controller to muscle 78, the controller will send a signal to muscle 78 that the applied load specified has been achieved and to discontinue further contraction. A similar process can take place when muscle 78 is instructed by the controller to reduce the applied load.

Figure 6:
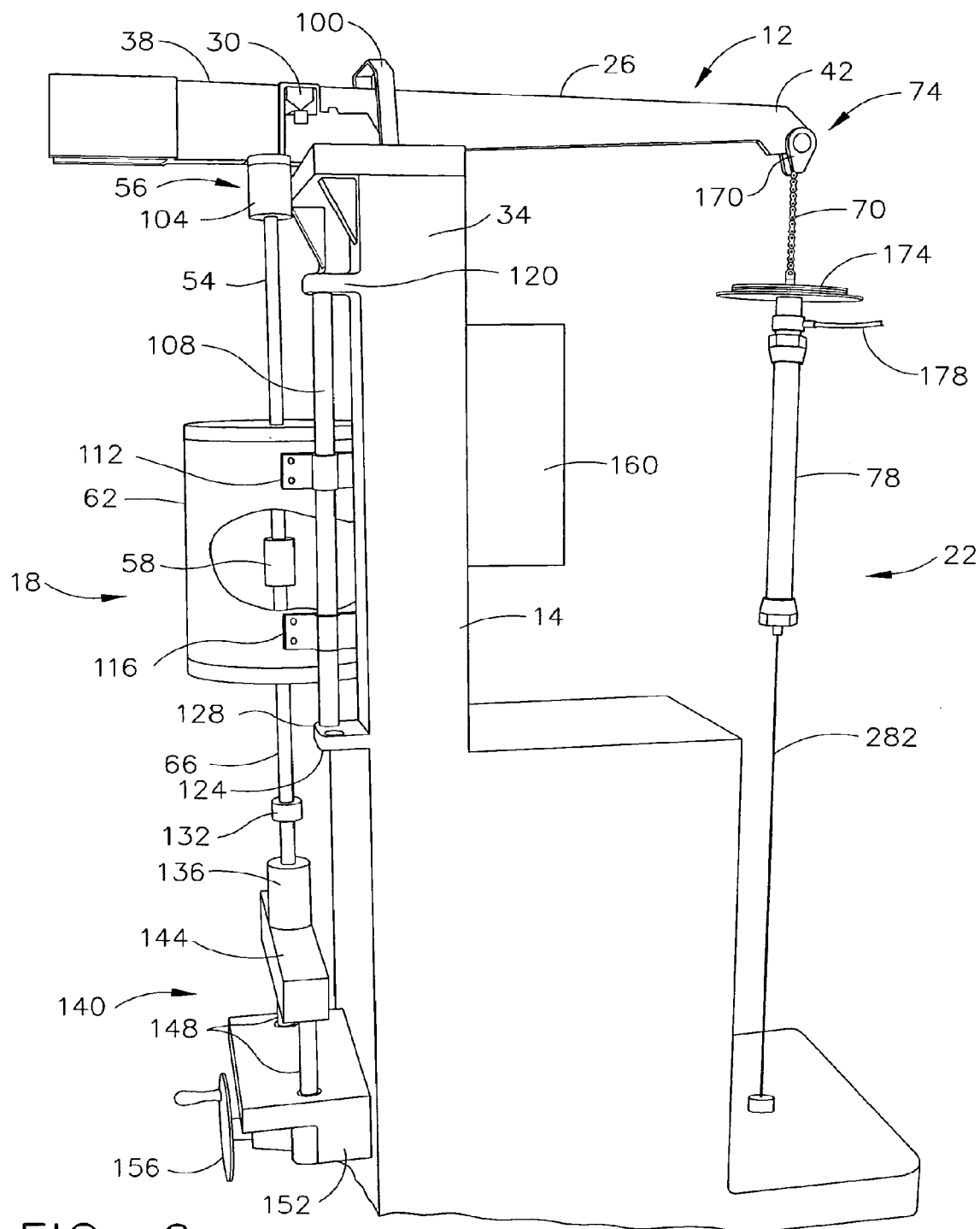
FIG. 6 is a more detailed perspective view with portions broken away of an apparatus that can be used in the "closed loop" system of FIG. 5.
Figure 7:
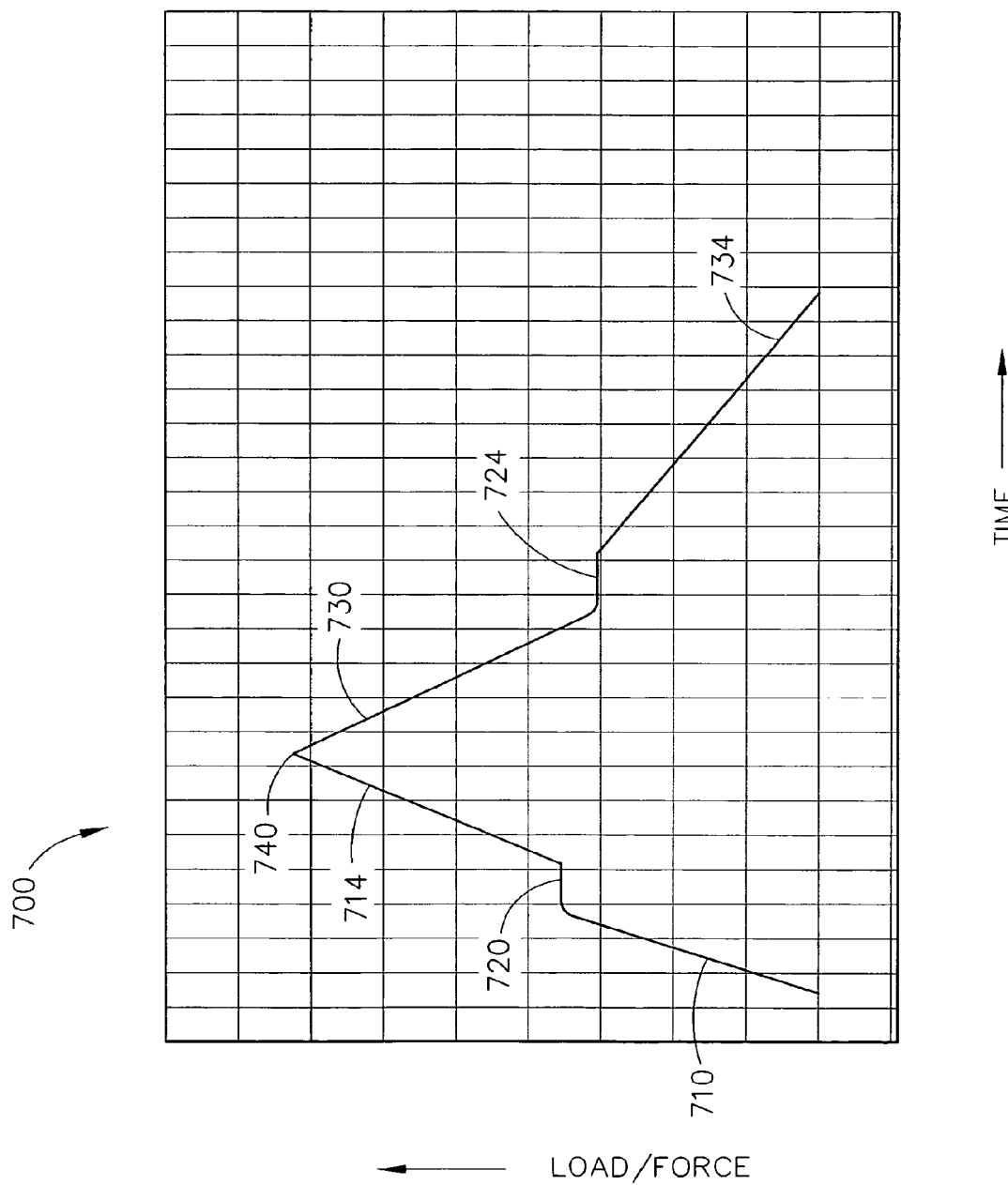
FIG. 7 is an illustrative graphical plot of a mission cycle test that can be carried out using the system and apparatus of FIGS. 5 and 6.

FIG. 7 is an illustrative graphical plot indicated generally as 700 of a possible mission cycle test that can be carried out using the system and apparatus of FIGS. 5 and 6. One possible test cycle of graphical plot 700 is shown in FIG. 7 that is intended to simulate the "real life" conditions experienced by components, parts, materials or operating equipment (e.g., a gas turbine engine) during use in the field. As shown in FIG. 7, graphical plot 700 can have a plurality of sequential loading (load increasing) phases indicated by upward slopes 710 and 714, a plurality of holding (sustained load at a specified level for a discrete period of time) phases indicated by plateaus 720 and 724, a plurality of sequential reducing (load decreasing) phases indicated by downward slopes 730 and 734, and a peak applied load phase point indicated as 740. As suggested by upward slopes 710 and 714, as well as downward slopes 730 and 734 of FIG. 7, the load can be applied and/or reduced at different rates to more closely simulate "real life" conditions.

While specific embodiments of the this invention have been described, it will be apparent to those skilled in the art that various modifications thereto can be made without departing from the spirit and scope of this invention as defined in the appended claims.

What is claimed is:

1. A system which cyclically applies and reduces a load on a test specimen to thereby subject the test specimen to cyclic testing, wherein the system comprises a fluidic mechanical muscle having a sheath with a flexible mesh secured at each end of the sheath and a bladder disposed within the sheath that inflates to cause contraction of the fluidic mechanical muscle and deflates to cause extension of the fluidic mechanical muscle to cyclically apply and reduce the load on the test specimen.

2. The system of claim 1 which further comprises a load train section associated with the test specimen, a load adjusting section associated with the fluidic mechanical muscle, and a mechanism for applying and reducing the load from the load adjusting section to the load train section to cause the load to be applied or reduced on the test specimen.

3. A system which cyclically applies and reduces a load on a test specimen to thereby subject the test specimen to cyclic testing, wherein the system comprises a fluidic mechanical muscle having a sheath with a flexible mesh secured at each end of the sheath and a bladder disposed within the sheath that inflates to cause contraction of the fluidic mechanical muscle and deflates to cause extension of the fluidic mechanical muscle to cyclically apply and reduce the load on the test specimen, a load train section associated with the test specimen, a load adjusting section associated with the fluidic mechanical muscle, and a mechanism for applying and reducing the load from the load adjusting section to the load train section to cause the load to be applied or reduced on the test specimen, wherein the mechanism comprises a pivoting lever arm and a frame, and wherein the lever arm extends generally horizontally and pivots on the frame.

4. The system of claim 3 wherein the load train section and the load adjusting section extend generally vertically.

5. The system of claim 1 which further comprises an environmental chamber for enclosing the test specimen.

6. The system of claim 1 wherein the system is a closed loop system and wherein the mechanical muscle is directly associated with a frame.

7. The closed loop system of claim 6 which comprises a feed back mechanism that provides a substantially linear and proportional application or reduction of the load on the test specimen.

8. The system of claim 1 which is an open loop system.

9. The system of claim 1 which further comprises a creep-rupture frame.

10. The system of claim 1 wherein the load applied on the test specimen varies substantially linearly when the fluidic mechanical muscle contracts.

11. The system of claim 1 wherein the load on the test specimen varies substantially linearly when the fluidic mechanical muscle expands.

12. A system which cyclically applies and reduces a load on a test specimen to thereby subject the test specimen to tensile testing, wherein the system comprises a mechanism for decoupling at least a portion of the load from the test specimen when the load is reduced and a fluidic mechanical muscle having a sheath with a flexible mesh secured at each end of the sheath and a bladder disposed within the sheath that inflates to cause contraction of the fluidic mechanical muscle and deflates to cause extension of the fluidic mechanical muscle to cyclically apply and reduce the load on the test specimen.

13. The system of claim 12 wherein the mechanism comprises a flexible link connected to the load.

14. An apparatus, which comprises:
   a. a frame;
   b. a load train section associated with the frame for subjecting a test specimen to a load;
   c. a load adjusting section associated with the frame comprising a fluidic mechanical muscle having a sheath with a flexible mesh secured at each end of the sheath and a bladder disposed within the sheath that inflates to cause contraction of the fluidic mechanical muscle and deflates to cause extension of the fluidic mechanical muscle for applying and releasing the load, and a mechanism for decoupling at least a portion of the load from the test specimen when the load is released; and
   d. a lever arm associated with the frame and having load train end adjacent and connected to the load train section and a load adjusting end adjacent to and connected to the load adjusting section, the lever arm being configured to apply and reduce the load from the load adjusting section to the load train section.

15. The apparatus of claim 14 wherein the mechanism is a flexible link connected to the load.

16. The apparatus of claim 14 wherein the flexible link is connected to the fluidic mechanical muscle.

* * * * *